United States Patent [19]
Vekstein et al.

[11] Patent Number: 5,134,639
[45] Date of Patent: Jul. 28, 1992

[54] OPTICAL COMMUNICATION LINK

[75] Inventors: Uri Vekstein, Haifa; Simha Levene, Doarna; Dan Zehavi, Haifa, all of Israel

[73] Assignee: Elscint, Ltd., Haifa, Israel

[21] Appl. No.: 543,433

[22] Filed: Jun. 26, 1990

[30] Foreign Application Priority Data

Jul. 3, 1989 [IL] Israel ............................ 090853

[51] Int. Cl.⁵ .......................................... H05G 1/60
[52] U.S. Cl. .................................. 378/15; 378/19; 378/196; 250/551
[58] Field of Search ............... 455/603, 617; 378/15, 378/19, 196; 250/551

[56] References Cited

U.S. PATENT DOCUMENTS

| | | | |
|---|---|---|---|
| 4,259,584 | 3/1981 | Krumme | 378/15 |
| 4,323,781 | 4/1982 | Baumann et al. | 378/15 |
| 4,427,983 | 1/1984 | Kruger et al. | 343/763 |
| 4,538,125 | 8/1985 | Beckmann et al. | 378/15 |
| 4,555,631 | 11/1985 | Martens | 250/551 |
| 4,794,796 | 1/1989 | Conte | 73/751 |
| 4,796,183 | 1/1989 | Ermert et al. | 378/15 |
| 4,912,735 | 3/1990 | Beer | 378/15 |

FOREIGN PATENT DOCUMENTS 2113690  9/1972  Fed. Rep. of Germany .

Primary Examiner—Janice A. Howell
Assistant Examiner—Don Wong
Attorney, Agent, or Firm—Sandler, Greenblum & Bernstein

[57] ABSTRACT

An optical communication link coupling a rotating part of a gantry of a computerized tomographic scanner to the stationary part of the gantry. The link comprises an arcuate hollow light conductor having one part rotating with the rotor of the gantry and the other part fixed to the stator of the gantry. Signal bearing light beams are transmitted into the link and are subsequently received from the link after transversing at least a portion thereof.

24 Claims, 7 Drawing Sheets

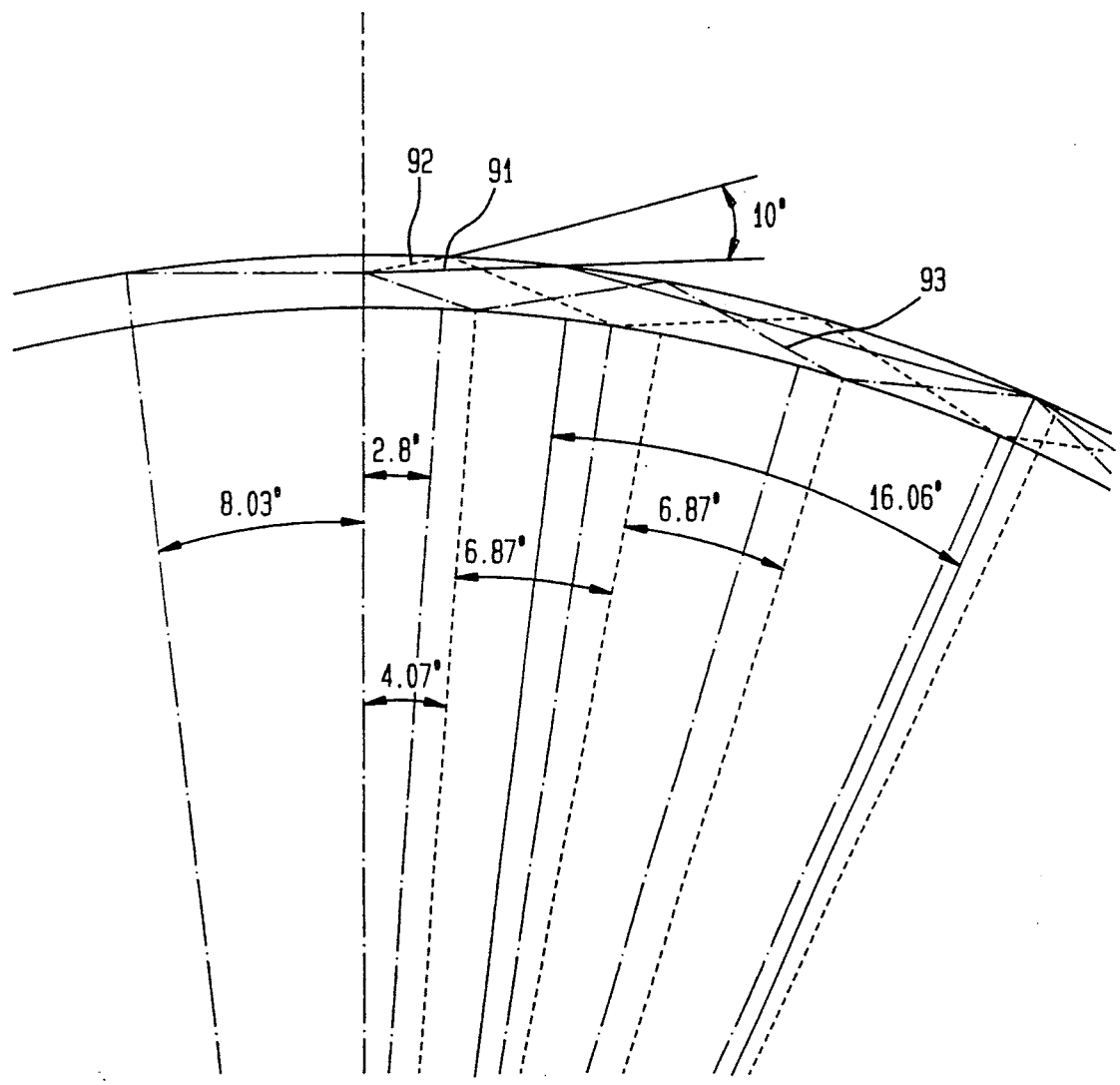

OPTICAL COMMUNICATION LINK

FIELD OF THE INVENTION

The present invention relates to data transmission apparatus particularly for a CT scanner to efficiently and reliably transfer data and/or control signals between a stationary member and a rotatable member.

BACKGROUND OF THE INVENTION

Most computerized tomographic (CT) scanners in present use are designed to operate as either "rotate-rotate" ("third generation") scanners or "rotate-only" ("fourth generation") scanners. A "rotate-rotate" scanner is one in which both the X-ray tube and the detector array are mounted on a common rotor that is rotatable on a stationary member about a central axis. A "rotate-only" scanner is one in which only the X-ray tube is rotatable on a stationary member about a central axis. In both cases, the stationary member is provided with a central axial aperture concentric with the axis of rotation of the X-ray tube. The aperture has an axial length greater than the height of a normal person and a diameter sufficient to enable a prone patient to be moved into and out of the scanner along its central axis. As a result of this configuration in the third generation scanners, the X-ray tube is mounted on a rotatable ring that is supported on bearings carried by a stationary ring on the stationary member.

In the rotate-rotate scanner, to operate the X-ray tube, electrical power in the range of 20-60 KW must be transferred to the rotatable member and the final operating voltage in the range to 100-150 KV must be supplied to the tube. In addition data from the detector array in the rotate-rotate scanners must be transferred to processing equipment that remains stationary. Control signals have to be supplied to the rotor to control operation of the X-ray tube, among other things. Conventionally, the required power and data (including control signals) are transmitted to and from the rotatable member via flexible high voltage cables for the power and shielded cables for the data. Cable uptakes or spooling systems are provided which enable at least one complete rotation of the rotatable member to occur.

More recently, new designs have been used for transferring both data and power to and from the rotatabale member. See, for example, the Patent Application entitled "Power Transfer Apparatus Particularly for CT Scanner", which was filed in the U.S. on Jul. 18, 1988, and received Ser. No. 200,680. That Application describes a unique inductive power transfer method which enables discarding the use of the flexible cables and spooling systems for the transmission of power.

Data transmission devices are found, for example, in U.S. Pat. No. 4,794,796, which covers a system that transmits data from a rotating device to a stationary part through a rotating wave guide.

Another data transmission device is described in U.S. Pat. No. 4,259,584. There data generated by the detector of a CT scanner is transmitted to stationary processing equipment using a ring of light conducting material bent around the center of rotation of the rotatable member. A light source emits light signals corresponding to the data signals transmitted onto the surface of a ring of light conducting material. The ring conducts the light signals over its entire circumference and has a coupling location at which a light receiver is arranged on the stationary part of the scanner.

Other rotating data transmission devices specially designed for the use with CT systems are disclosed in U.S. Pat. No. 4,323,781 and U.S. Pat. No. 4,427,983 wherein the data to be transmitted from a rotating annular part to a stationary annular part is achieved by discreet pluralities of transmitters and receivers.

Optical communication links using hollow tubes have not been used because of the difficulties of constructing such tubes with proper surfaces. Proper surfaces must be highly reflective and smooth to assure that the angle of reflectance to the wall of the tube in general is equal to the angle of incidence to the wall of the tube with a minimal of light diffusion. Even if the inner periphary of the hollow tube had the proper surface, it was widely believed by those skilled in the art that the hollow tube having an arcuate shape necessary to mount the tube about the rotor would cause light ray divergence. Such divergence would, of course, increase the number of reflections and thereby attenuate the intensity of the light reaching light receivers. The intensity of light at the receiver is given by the equation:

$$I_r = I_o R^n$$

where:
  $I_o$ = the original intensity of the light
  R = reflectance, and
  n = number of reflections.

Since R is a fractional value, it is apparent that as the number of reflections increase the light intensity at the receiver decreases drastically. Because the divergence of light beams in light conductive material is minimized and the reflectance is relatively high, such materials though expensive, have been the material of choice for optical communication links, especially where the path is curved and the light is incoherent.

In summary then, the prior art shows the transmission of data and control signals using either light conductive material curved around the centre of rotation (for example, U.S. Pat. No. 4,259,584) or a rotatable wave guide having transmitters coupled thereto that is mounted on the rotor with receivers mounted on the stator. (See, for example, U.S. Pat. No. 4,796,183). More receivers than transmitters are used to enable utilization of more than one "channel" in the wave guide at the same time. Wave sinks are provided to divide the circular wave guide into a plurality of sub-paths. The patent explains that in case of transmitting from the stator to the rotor, then the wave guide would be mounted on the stator and along with the transmitters while the receivers would be mounted on the rotor. Hence, according to the patent, the wave guide is mounted either to the stator or to the rotor or there is a wave guide mounted to the stator and another wave guide mounted to the rotor for transmission of control and data signals, respectively to and from the stator. The prior art requires either a multiplicity of complicated wave guides or solid light transmitting material rotating with the rotor about the stator axis for the transmission and receipt of data and control signals.

Thus, the prior art does transmit control and data signals to and from the rotating part of the gantry in a manner enabling continuously rotating the gantry over many revolutions without having to reverse and return to the zero degree point as was required when cables were used for coupling the rotary part of the gantry to the stationry part of the gantry. However, the prior art used for transmitting signals to and from the rotary part of the CT gantry requires complicated and expensive microwave or solid light transmitting materials.

BRIEF DESCRIPTION OF THE INVENTION

Accordingly, it is an object of the present invention to provide for communicating data and control signals between the rotary part and the stationary parts of a CT gantry in a simple, effective and inexpensive manner.

A feature of the invention enables the transmission of both control signals from the stationary part of the gantry to the rotary part of the gantry and data and/or control signals from the rotary part of the gantry to the stationary part of the gantry using a hollow light conductor having specular inner surfaces. A portion of the specular surfaces of the hollow light conductor rotates and a portion of the specular surfaces of the hollow light conductor is stationary.

In accordance with a broad aspect of the present invention, an optical communication link coupling a rotating part and stationary part is provided. The communication link includes communicating means for transmitting data and control signals between said stationary part and said rotary part, said communicating means comprising:

a hollow light conductor for transmitting light signals, means for converting electrical signals to light signals, means for coupling said light signals to said hollow light conductor.

means for coupling said light signals which have passed through at least a part of said light conductor from said light conductor, means for converting said light signals from said light conductor to electrical signals, and means for using said electrical signals either for data processing to provide images or for control purposes.

A feature of the present invention comprises an arcuate hollow light conductor having a rectangular cross section divided into parts, one part rotating with the rotor of the CT gantry and the other part being stationary with the stator of the CT gantry. On one wall of the hollow light conductor, either the rotating or stationary side, depending upon the direction of the flow of information; i.e., data signals and/or controls signals, are a plurality of light generating transmitters mounted along the circumference of the hollow light conductor. Opposite each transmitter within the hollow light conductor, a mirror inclined at an angle such as 45° is provided to project transmitted light beams into the light conductor in a direction substantially parallel to the tangent to the circle coaxial to the arcuate hollow light conductor at the point where the light beam strikes the mirror. After traversing at least a portion of the light conductor, the transmitted beams are reflected on to a light detector or receiver by a mirror within the hollow light conductor also inclined at an angle such as 45°.

The optical communication link preferably includes a plurality of such hollow light conductors. The cross section of each of the hollow light conductor is preferably a rectangle. The inner sides of the walls of the hollow light conductors are smooth and highly reflective.

A further feature of the hollow light conductor is the use of lenses to increase the intensity of the light beams coupled out from the light conductor. The use of lenses are possible because of the low rate of divergence of the light beams in travelling through the light conductors.

In a preferred embodiment attached to the inner walls of the hollow light conductor is a film of aluminized MYLAR (polyethylene terephthalate) mounted on a polystyrene base. The aluminized MYLAR is smooth and has a reflectance of about 0.98. The polystyrene base implements attaching the reflective MYLAR onto the inner walls of the light conductor. Thus, an inexpensive but highly reflective and efficient hollow light conductor is provided. Preferably approximately half of the reflective walls are attached to the stator and approximately half of the reflective walls are attached to the rotor of the CT gantry.

According to another feature of the invention the light transmitting means includes a light emitting diode (LED) and the light detecting or receiving means includes a photo sensitive diode (PSD).

According to a further feature of the present invention each of the plurality of light guides can be divided into at least two channels for simultaneously receiving and/or transmitting data or control signals. That is, each channel can either transmit or receive signals (date or control) simultaneously with the other channel. Thus, for example, in a preferred embodiment seven such hollow light conductors are provided between the stator and the rotor. Accordingly, there are at least 14 channels for communication.

BRIEF DESCRIPTION OF THE DRAWINGS

The above named and other features and objects of the present invention will be best understood when considered in the light of the following description made in conjunction with the accompanying drawings, wherein:

FIG. 9 is a ray tracing to aid in explaining the unique optical characteristics of the hollow light conductor.

GENERAL DESCRIPTION

Figure 1:
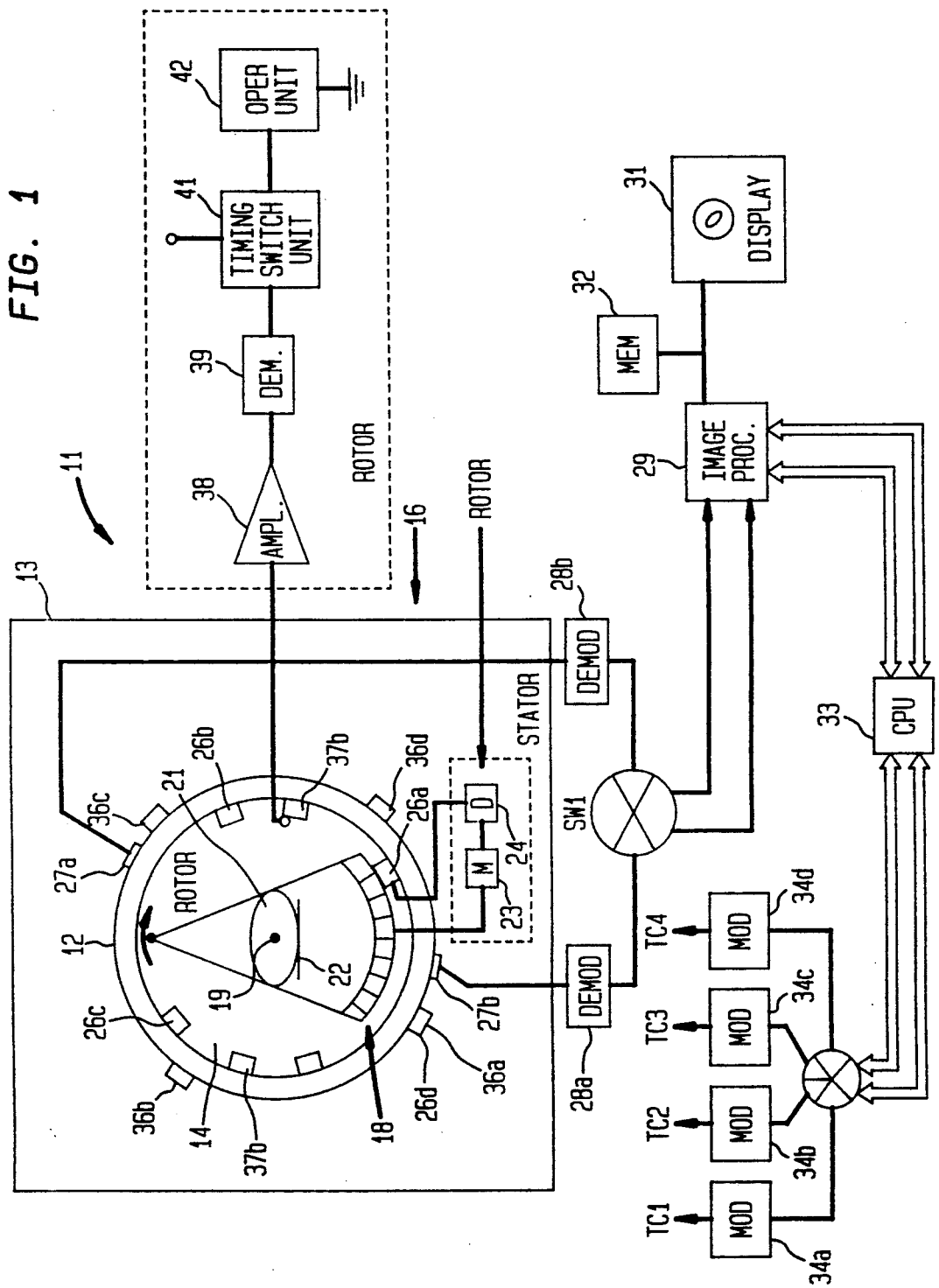
FIG. 1 is a block diagram of an optical communication link between the stator and the rotor of a gantry in a computerized tomographic (CT) scanner.

FIG. 1 shows in block diagram form a CT system generally designated as 11. The invention is concerned with those parts of the CT system relating to the optical communication link 12 between the stator 13 and the rotor 14 of the CT system. The rotor and the stator of the CT system together comprise a gantry 16. The rotor of the gantry includes the X-ray source 17 and the detector array 18. The rotor rotates about a central axis rotation 19 and thereby provides patient density data responsive to X-rays which pass through a patient 21 lying on a bed 22 within the gantry to impact on the detectors of the detector array 18.

In this manner density data is acquired during the rotation of the rotor about the patient. The rotation of the rotor about the patient enables X-rays from the source to pass through the patient at different angular positions and impact onto the detector array 18.

The detector array 18 is comprised of a plurality of individual detectors. The detectors convert the detected X-rays to electrical signals after the X-rays have passed through the patient at plurality of points. The attenuation of the X-rays by the patient's body assure that the detected X-rays are of varying intensity. The detected X-rays are processed to provide an X-ray image.

In the past, the detected signals were transmitted to the data processing equipment through cables. The use of cables for connecting the rotating part of the gantry to the stator and/or control and processing equipment is a limitation on the freedom of motion of the rotor of the gantry. With cables, after each 360° rotation about the central axis the rotor had to be returned to the zero position to keep the cable from entangling and breaking.

In the previously filed patent application noted hereinabove provisions are made for coupling the power components of the rotor to the stator without the use of cables. Accordingly, by coupling the data and control signals to the rotor through an optical communication link the continuous rotation of the rotor about the patient is made possible. That is, no longer is the rotor inhibited and bound to rotate only one revolution. The communication of the data and control signals between the rotor and the control and processing equipment which are part of the CT system is accomplished using the unique optical communication link 12.

Data from each of the detectors of the detector array 18 is transmitted through a modulator or encoder 23. From the encoder 23, the encoded signal is sent to a distributor or multiplex unit 24. From the multiplex unit 24 the data and/or control signals are provided to light transmitting means 26. In actual practice a plurality of transmitters are provided. They are indicated by the four transmitters (TD) 26a-26d. The transmitters are all connected to the distributor 24. However, in the interest of clarity, the connecting lines from the transmitters TD to the distributor 24 are only indicated by arrows.

The transmitters are shown in the drawings as being located on the rotary side of the communication link. On the stator side of the communication link a plurality of light receivers are provided. They are indicated by the two light receivers RD, reference numberals 27a and 27b. In a preferrd embodiment the light receivers are separated by 180° and the light transmitters are separated by 90°.

The receivers 27a and 27b are connected to demodulators or decoders 28a and 28b respectively. The decoders are coupled through switching means SW1 such as a multiplexer to an image processor 29. The decoded signals are processed in the usual manner well known to those skilled in the CT art to provide an image on monitor 31. The image processor 29 works with a memory 32 and along with other units in the CT system receives control and timing signals from a central processing unit (CPU) 33. The image processor 29 includes units well known to those skilled in the art for providing images from the detector array data, such as, for example, amplifiers, digital-to-analog converters and back projection means. Similarly, the decoders shown at 28a and 28d include well known circuitry such as amplifiers and analog-to-digital converters.

To couple control signals from CPU 33 to components on the rotor the two-way optical communication link is used. Also, the light transmitters and the light receivers that are integral parts of the two-way optical communication link of the present invention are controlled by control signals originating in the CPU 33.

The contorl signals from CPU 33 are transmitted through a switching unit SW2 which may be a multiplexer and is shown connected to a plurality of modulators or encoders 34a-34d. The encoders are connected to transmitters 36a-36d on the stator of the gantry. Thus, encoded signals from encoders 34a-34d are coupled through the control signal transmitters 36a-36d mounted on the stator side of the optical communication link 12. The trasmitted control signals are carried by the optical communication link to a pair of receivers 37a and 37b, indicated as control signal receivers RC shown mounted 180° apart on the rotor.

The equipment for operating on the received control signals is shown in FIG. 1. Therein the receiver 37b is shown, for example, as being connected to amplifier means 38 for amplifying the received signal. The amplified received control signal is decoded or demodulated in decoding or demodulating unit 39. The decoded signals may be used to operate timing switch unit means 41 and/or control the operation of an operating unit such as, for example, the X-ray tube 42.

Accordingly, the optical communication link is a two-way communication link. It couples data and/or control signals between the detector array and the processing circuitry and between the CPU of the system and various units on the rotor. Both data signals and control signals can be sent simultaneously in accordance with the unique optical communication link provided.

Figure 2:
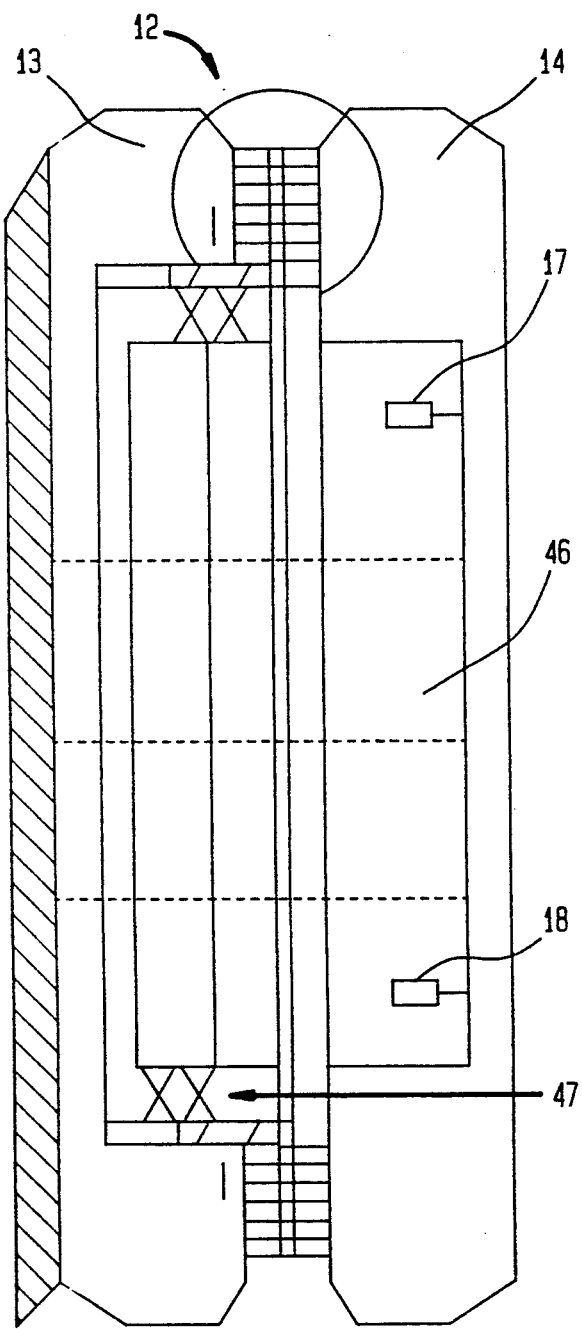
FIG. 2 is a sectional view of the rotor and stator of the CT scanner of FIG. 1 including the optical communciation link comprised of hollow light conductors.

In FIG. 2 the optical communication link 12 is shown as mounted to both the rotor unit 14 and the stator unit 13. Optical communication link as shown in FIG. 2 comprises a plurality of hollow light conductors having rectangular cross sections.

Both the rotor and stator are shown as having a bore 46 for receiving the patient therein. In addition on the rotor the X-ray source 17 and the detector array 18 are indicated. The rotor itself rotates on roller bearings indicated at 47 located between the rotor and the stator. The optical communication link 12 is in a circle designated "A". Details of the optical communication link of circle A are better seen in FIG. 3.

Figure 3:
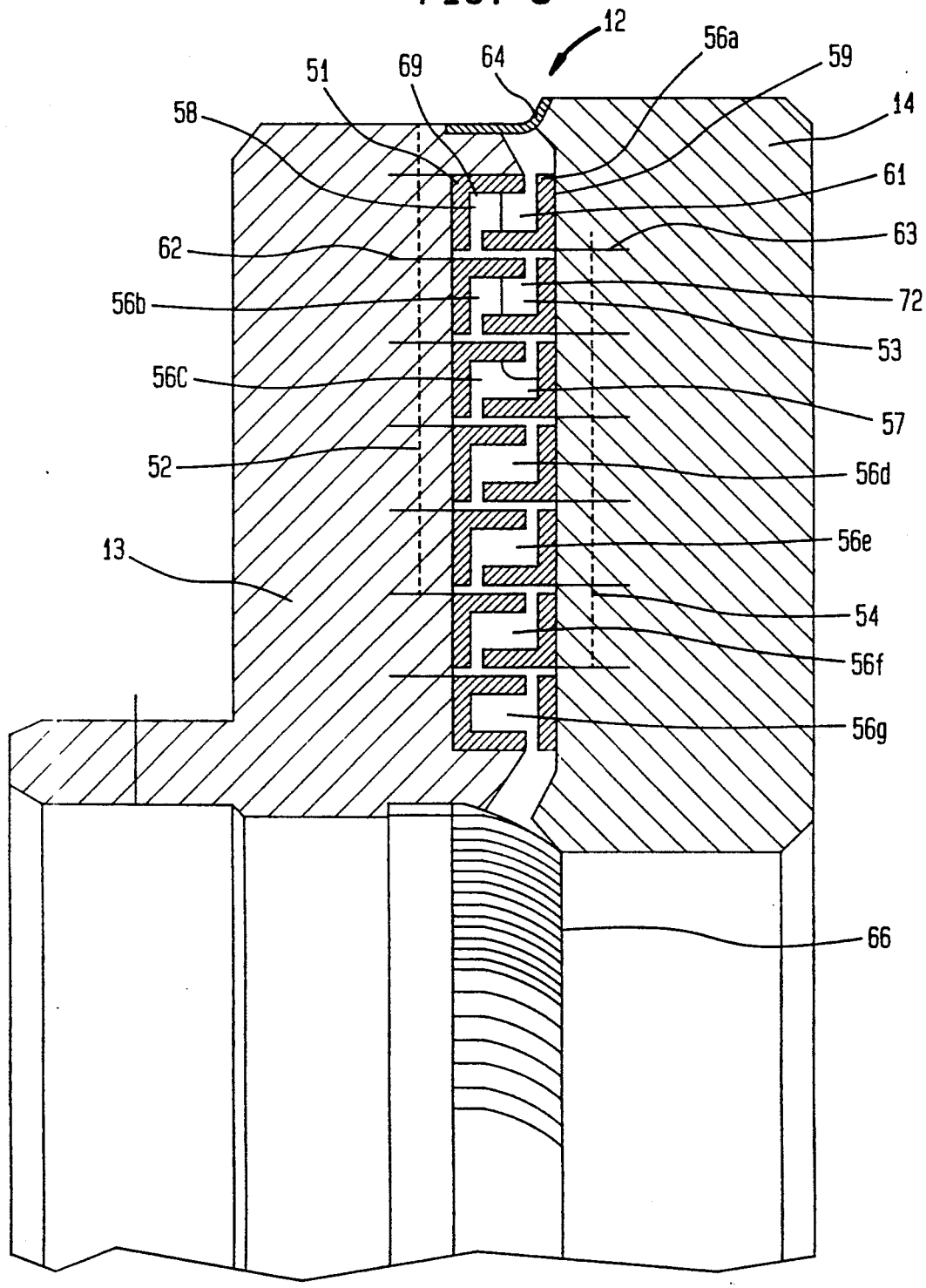
FIG. 3 is a magnified sectional showing of the optical communication link 12 shown in the part of FIG. 2 enclosed in circle A.

FIG. 3 shows the optical communication link 12 as having a part thereof integral to the stator 13 and a part thereof integral to the rotor 14. Also shown in FIG. 3 in dashed line form are a light encoding and transmitting unit operating as a data signal transmitter [TD] indicated by reference number 26a and an encoded light signal receiver RD indicated by reference unit 27a.

The signal transmitter which converts encoded electrical signals to encoded light signals comprises a light emitting diode (LED) 51 along with amplifying and modulating or encoding circuitry mounted on a circuit board 52. Similarly, the receiver unit 27a which converts light signals to electrical signals includes a photo sensitive diode (PSD) 53 mounted on a PC board 54 that has thereon amplifying and decoding or demodulating circuitry well known to those skilled in the art. There are shown in the preferred embodiment of FIG. 3 seven distinct hollow light conductors 56a–56g which are included in the optical communication link.

Each hollow light conductor comprises strips of reflective material attached to the stator such as the strips of reflective material 57 and 58 attached at right angles to each other along the stator. In addition there are strips of reflective material 59 and 61 attached to the rotor. The strips of reflective material line the inner walls defining a rectangular cross section that is mirror like. Thus, light in the conductor is reflected from the inner walls as the light proceeds through the conductor. The strips that are shown oriented normally to the rotor and stator; i.e., the top and bottom strips are attached to partitions such as partitions 62 and 63 which extend perpendicular to the face of the stator and the rotor. The partitions are preferably made of spring steel.

In a preferred embodiment each of the hollow light conductors has an average diameter of about 880 mm. The cross section of each light conductor is a rectangular hollow section of 7×10 mm with the 10 mm being the distance between the reflective material attached to the faces of the rotor and the stator. The 7 mm is the distance between the reflective material attached to the partitions such as partitions 62 and 63. In a preferred embodiment the reflective material is made of a polystyrene base with a polyethalene terphthalate film attached thereto and having vacuum evaporated aluminum deposited thereon. The total thickness of the material making up a reflective surface is approximately 1 mm.

Means are provided for maintaining the hollow light conductors of the optical communication link dust-free. More particularly, dust inhibiting brushes such as brush 64 shown at the top of the hollow light conductors and dust inhibiting brushes 66 shown at the bottom of the hollow light conductors tend to prevent the entrance of dust into the hollow light conductors.

Figure 4:
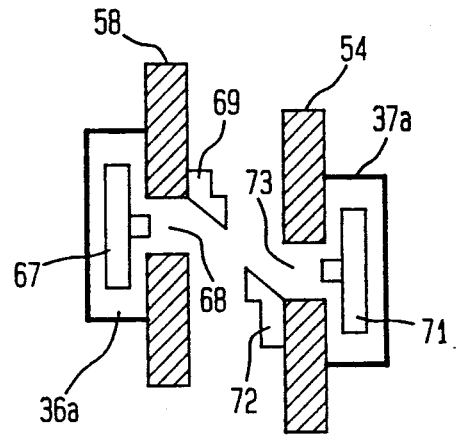
FIG. 4 is a sectional view taken along line 4—4 in FIG. 3 and looking in the direction of the arrows.

FIG. 4 illustrates in greater detail the mechanism for transferring light beams to and from the hollow light conductors. More particularly, in FIG. 4 a signal transmitter such as unit 36a is shown juxtaposed to an opening in the top hollow light conductor. Unit 36a comprises a printed circuit board indicated at 67 on which are mounted various components for encoding the control signals and a light sensitive diode (LED). Light is generated by the LED responsive to the encoded control signals and is transmitted through aperature 68 in the strip 57 of reflective material. The light strikes mirror 69. The mirror 69 is preferably at 45° to the longitudinal side walls (or strips such as strips 58, 59) of the hollow light conductor. Thus, light is directed into the hollow light conductor and extends circumferentially along the hollow light conductor.

As shown, attached to the rotor is a signal receiver unit 37a. The unit comprises a PC board indicated at 71 on which are mounted components for decoding received light beams and a photo sensitive diode. PSD 1. The light beam 56a travelling in the hollow light conductor, strikes a receiving mirror 72. The receiving mirror preferably has an angle of 45° to the longitudinal side wall of the light conductor. The receiving mirror directs the light rays through aperture 73 onto photo sensitive diode PSD 1.

The aperture 73 is in the light reflecting material 59. A lents 75 may be mounted in the aperture. Preferably an f/2.2 lens is used. Due to a lack of divergence of the light beams, the lens could also be mounted before the mirror, for example, and even in the aperture traversed by the light in entering the hollow light conductor, and still operate efficaciously.

The transmitting mirror 69 in a preferred embodiment extends 4 mm into the hollow conductor from the top of the reflecting surface 58. The receiving mirror 72 has a height of 5 mm from the reflecting surface 59. There are 10 mm between surfaces 58 and 59. Accordingly, there is sufficient clearance for the mirror 72 on the rotor to pass the mirror 69 on the stator 69.

Figure 5:
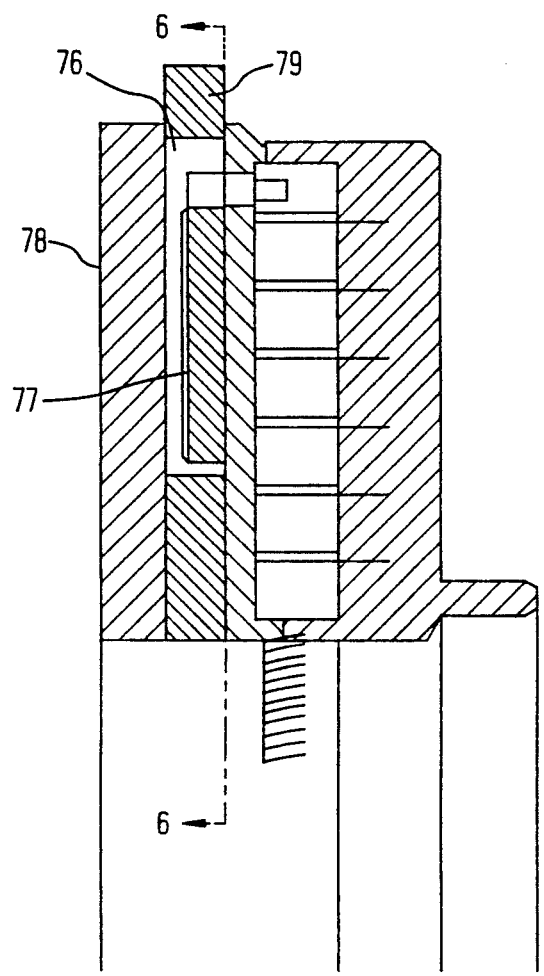
FIG. 5 is a sectional side view of the hollow light conductors with a light receiver or light transmitter mounted to one of the conductors.

FIG. 5 is another cross sectional view of the hollow light conductors. Shown therein is a mounting recess 76 in the stator side and either a control signal transmitting unit or a data receiving unit mounted in the recess 76. The light transmitting or light receiving unit is indicated generally by the reference numeral 77. Note that a flange 78 covers the recess 76 to help to protect the unit mounted in the recess and to prevent the entrance of dust into the hollow light conductors.

Figure 6:
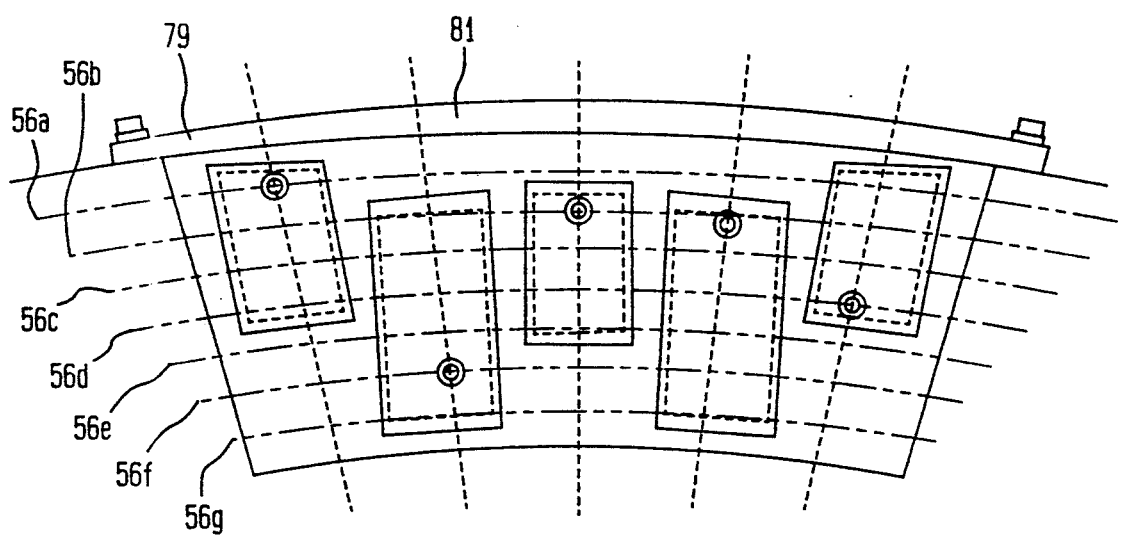
FIG. 6 is a plan view taken along line 6—6 of FIG. 5 and looking in the direction of the arrows.

FIG. 6 shows a plurality of transmitters and receivers mounted to receive and/or transmit light into the hollow light conductors. Each of the seven hollow light conductors are indicated by dash-dotted lines and bear the hollow light conductor reference numbers 56a–g. Note that the transmitters are depicted as being narrower than the receivers. Therefore, three transmitters indicated as T1, T2 and T3 and two receivers indicated as R1 and R2 are shown in FIG. 6. Each of the illustrated transmitters and receivers are shown as having their light transmitting or light receiving diodes coupled to different hollow light conductors. A cover plate 79 is shown for covering the recess 76. Leads for connecting the circuitry of the transmitters and receivers to the system are also indicated, for example, at 81.

Figure 7:
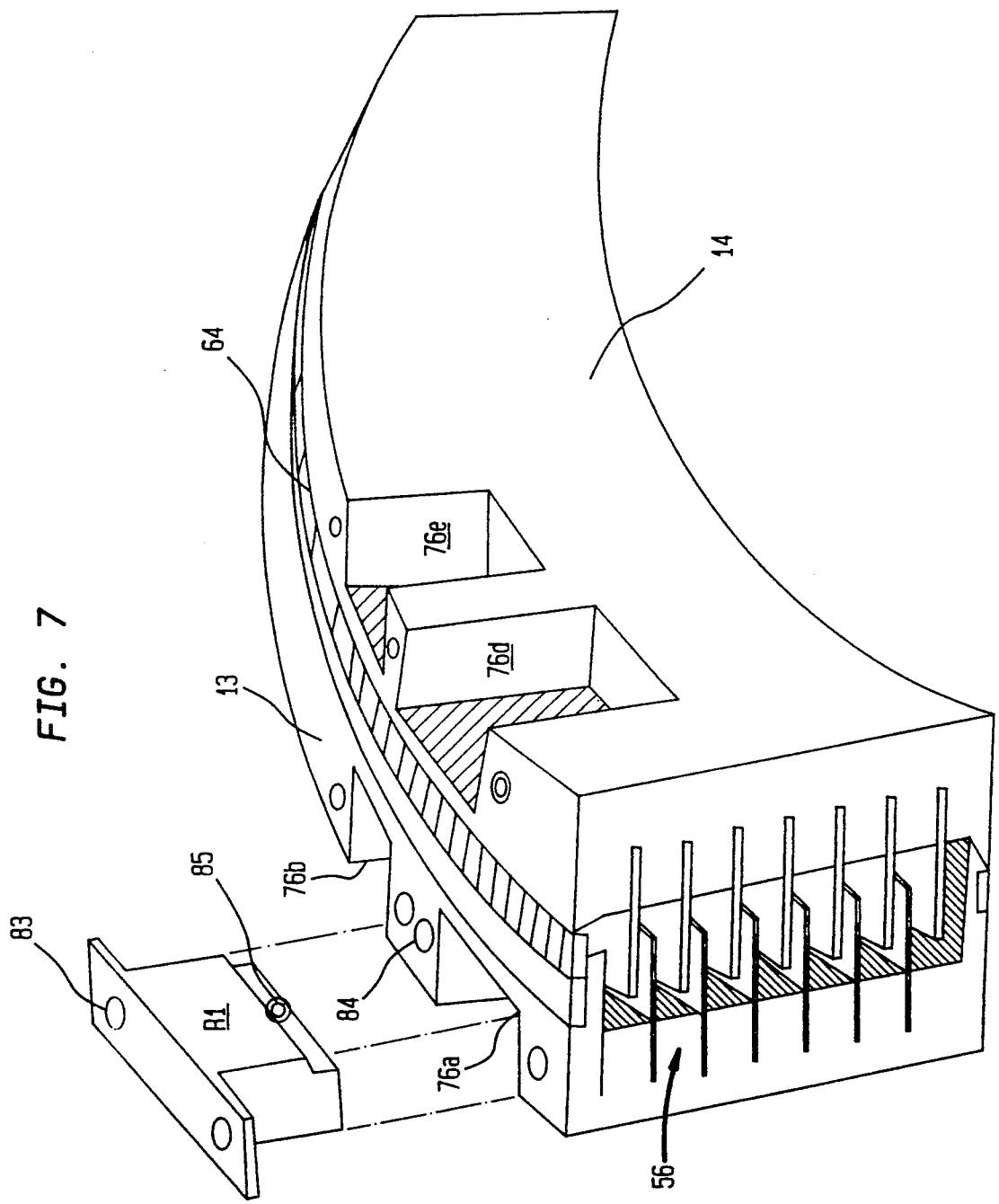
FIG. 7 is a pictorial view of the stator and the rotor with the hollow light conductors therein and showing a receiver unit exploded therefrom.

FIG. 7 is a pictorial showing of the stator 13 and rotor 14 with the curved hollow light conductors 56 and transmitting or receiving unit mounted in recesses 76a–e therein along with a light detecting or receiving unit R1. The top brushes for inhibiting the entrance of dust and dirt are shown at 64. The transmitting and receiving units are fixedly attached to the stator or the rotor with connecting means and apertures such as aperture 83 in the units aligned with apertures such as aperture 84 in the stator, for example. The location of the photo sensitive diode for unit R1 is indicated at 85.

Figure 8:
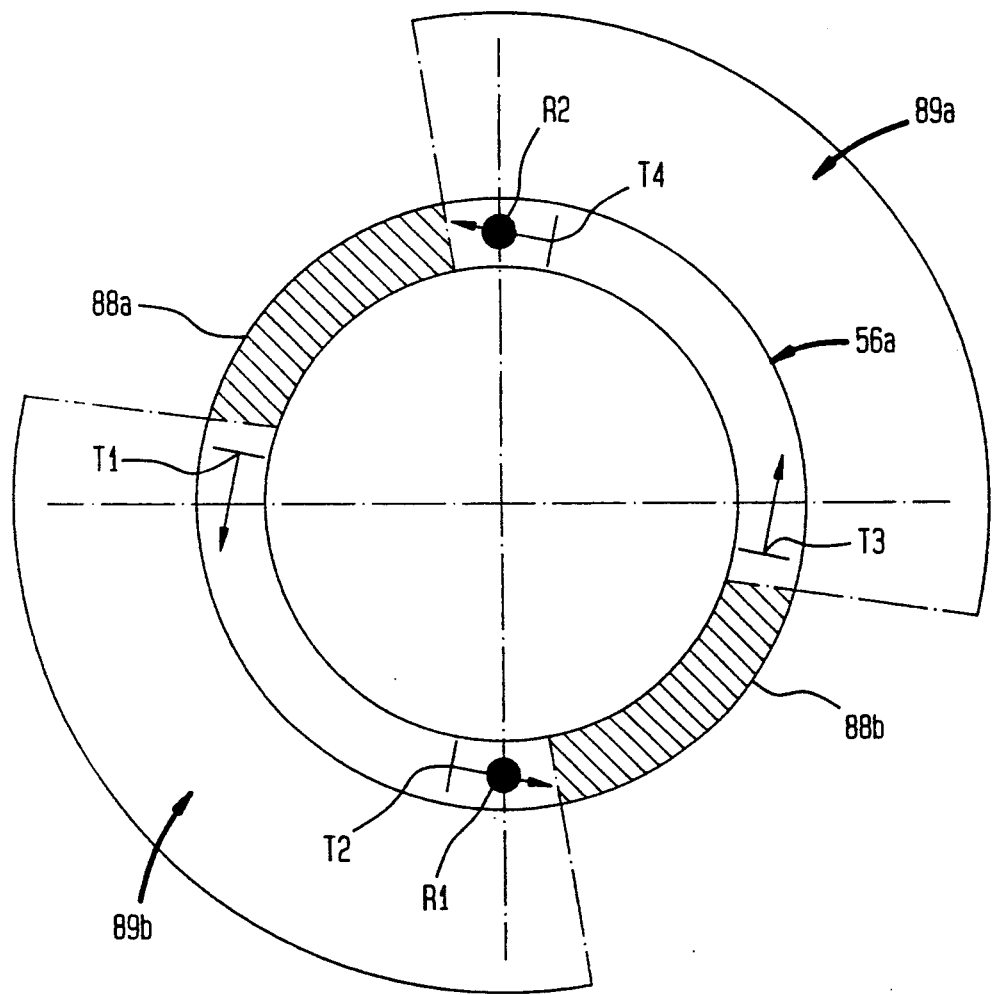
FIG. 8 is a schematic showing of one hollow optical light conductor with receivers and transmitters mounted thereon for providing dual channels of communication in the single hollow optical light conductor.

FIG. 8 illustrates a further feature of the invention wherein each of the hollow light conductors can be converted into two separate channels, each capable of simultaneously handling the transmission of separate information. For example, FIG. 8 shows hollow light conductor 56a comprising separate channels 86a and 86b. The light transmitters T1, T2, T3 and T4 which are each about 90° apart are mounted on the rotor. In the transmission mode, they transmit the data from the detector array on the rotor side of the hollow light conductor to the receivers R1 and R2 mounted about 180° apart on the stator. In the position shown in FIG. 8 transmitters T2 and T4 are each transmitting light encoded with data which is received by light receivers R1 and R2 respectively. Transmitters T1 and T3 are not turned on. Any light that goes past receivers R1 and R2 reaches blocked zones; i.e., a portion of the light conductor that does not have reflecting material. In fact, in a preferred embodiment, it has light absorbing material in place of the light reflecting material. The two blocked zones are shown as zones 87 and 88.

When transmitter T4 passes receiver R2 it is turned off and transmitter T3 is turned on. Similarly, when transmitter T2 passes receiver R1 it is switched off and transmitter T1 is switched on.

Each of the unblocked channels of the hollow light conductors can carry different information. Instead of each hollow light conductor forming a single channel each hollow light conductor forms a plurality of channels such as the two channels shown in FIG. 8 where the hollow light conductor 56a has two transmission zones 89a and 89b. Thus, the seven hollow light conductors become 14 channels for communicating information, data and control signals between the stator and the rotor.

The light tracing of FIG. 9 is indicative of the lack of divergence of the reflected beams in the hollow light conductor. The tracing assumes a light fan beam extending over an arc of ±10 degrees from the center line of an 8 mm wide hollow optical light conductor whose radius is 400 mm. Note that the central ray 91 (shown as a solid line) of the beam strikes the top or outer wall of the hollow optical light conductor after traversing a sector of 8.03 degrees. It is reflected from the outer wall and strikes the outer wall again after traversing a sector of 16.06 degrees without impacting on the bottom or inner wall. In fact, for rays within an inner cone of ±5 degrees the inner wall is unnecessary.

A central ray leaving at −8.07 degrees is tangential to the inner wall and, therefore, is reflected around the hollow light conductor with only one half the number of reflections. After the second reflection the central ray ricochets around the circular light conductor in a series of 22 sectors of 16.06 degrees. At no point around the circle does the central ray have an angle of incidence exceeding ±8.03 degrees.

The second ray 92 (shown as a dotted line) is shown moving to the right makes an outwardly going angle of 10 degrees to the central ray. It is reflected from the outer wall after traversing a 2.8 degree sector. Then it is reflected from the inner and outer walls traversing successive sectors all equal to 6.87 degrees. Again indicative of a suprising lack of divergence.

The third ray 93 (shown as a dashed line) also traverses sectors of 6.87 degrees after a preliminary 4.07 degrees. Thus, the number of reflections is minimal due to the particular geometry of the circular hollow light conductor which minimizes beam divergence.

In one preferred embodiment the LEDs are LEDs supplied by Motorola Catalog No. MF0E1203 or equivalent. The photo sensitive diodes are supplied by RCA Catalog No. C30808 or equivalent. The transmitter and receiver are purchased commercially from Fibronics Ltd. according to the following specifications:

Transmitter:
Maximum Input Current—150 MA
Data Rate (CDP)—10 MNz
Typical Output Power—1 MWatt (Odbm)
Differential Input Line Driver
Receiver:
Input Voltage—9-12 V
Maximum Line Current—TBD
Without Line Driver—TBD
Data Rate—10 Mbit/sec
Clock—10 MHz
Dynamic Range (Min.)—20 db
BER—$10^{-12}$
Differential Output Line Driver In operation a two-way optical communication link is provided that is ideally suited for transmitting control and data signals between the rotor and stator of a CT gantry; i.e., between the control and processing circuitry of the CT system and the control and data acquisition circuitry of the CT system. The two-way hollow optical communication link comprises a plurality of hollow light conductors. Each hollow light conductor is comprised of smooth highly reflecting surfaces mounted to both the stator and the rotor. Encoded light signals generated by light sources are transmitted into the hollow light conductor using means such as LEDs. The transmitted light is received by light sensitive solid state devices such PSDs accompanied by circuitry which decodes the encoded light signals. The circular hollow light conductors comprise reflective inner surfaces made of aluminized MYLAR having a reflectance coefficient of approximately 0.98.

An inexpensive, reliable and highly reflective surface is thus provided. Surprisingly, the curved top and bottom inner walls do not cause divergence of the light beams. The side walls are effectively straight parallel walls and, therefore, do not cause divergence.

A feature of the invention enables converting each of the hollow light conductors into a plurality of separate communication channels by dividing the hollow light conductors into light blocked zones and light transmission zones.

While the invention has been described using preferred embodiments, it should be understood that the description is exemplary only and not to be restrictive of the invention, which are defined by the accompanying claims.

What is claimed is:

1. A system for transmitting data between a rotating part and a stationary part comprising:
   a rotor,
   a stator,
   a hollow light conductor between said rotor and said stator,
   means for transmitting a light beam modulated responsive to information to be transferred between said rotor and said stator,
   means for receiving and demodulating said modulated light beam from said hollow light conductor after said modulated light beam has traversed at least a part of said hollow light conductor to obtain said information,
   means for using said information.

2. The system of claim 1 wherein the rotor and the stator are parts of a gantry for a computerized tomography system, the information includes data from X-ray detectors and the means for using the information includes image processing means for deriving an image from said data.

3. the system for transmitting data of claim 1 wherein said hollow light conductor is circular and coaxial with the rotor.

4. The system for transmitting data of claim 1 where part of said hollow light conductor is on said rotor and part of said hollow light conductor is on said stator.

5. The system for transmitting data of claim 1 wherein said hollow light conductor has a rectangular cross section.

6. The system for transmitting data of claim 5 wherein said hollow light conductor has inner walls describing said rectangular cross section, the inner walls of said rectangular cross section comprising smooth reflecting surfaces, said surfaces being sufficiently smooth to minimize diffusion of the reflective light.

7. The system for transmitting data of claim 6 wherein said smooth reflecting surfaces comprise aluminized polyethylene terephthalate.

8. The system of claim 6 wherein said aluminized polyethylene terephthalate is mounted on a polystyrene base and said polystyrene base is mounted on the inner surfaces of said rectangular cross section.

9. The system of claim 1 wherein said hollow light conductor means has a rectangular cross section and comprises side walls and top and bottom walls, one of said side walls being integral to said stator, the other of said side walls being to integral said rotor, one of said top and bottom walls being integral to the stator and the other of said top and bottom walls being integral to the rotor.

10. The system of claim 9 wherein said top and bottom walls comprise partial partitions extending from said rotor into the space between said rotor and said stator towards said stator and from said stator toward said rotor into the space between said rotor and stator.

11. The system of the claim 10 wherein said partial partitions comprise spring steel.

12. The system of claim 1 wherein said means for transmitting a modulated light beam into said hollow light conductor comprises means for generating a light beam and first mirror means for directing the light beam into the hollow light conductor.

13. The system of claim 1 wherein said means for receiving and demodulating said modulated light beam from said hollow light conductor comprises second mirror means.

14. The system of the claim 13 wherein said first and second mirror means are mounted at 45° to the side walls.

15. The system of claim 13 wherein said means for demodulating said modulator light beams includes photo sensitive diode means for detecting said light beam directed out from said hollow light conductor by said second mirror means.

16. The system of the claim 13 wherein said means for directing said light beam out from said hollow light conductor includes first lens means.

17. The system of claim 16 wherein said means for directing said modulated light beam into said hollow light conductor includes second lens means between said light beam generator and said hollow light conductor.

18. The system of claim 1 wherein lens means are included in the hollow light conductor.

19. The system of claim 1 wherein means are provided for dividing each hollow light conductor into a plurality of hollow light conductor channels separated by light blocking sections.

20. The system of the claim 19 wherein a plurality of said transmitters and receivers are mounted to communicate in the light conducting sections of the channels.

21. The system of claim 20 where a pair of receivers are mounted on the stator substantially 180° apart in light conducting sections juxtaposed to light blocked sections on the parts of the hollow light conductor mounted on the stator, four transmitters are mounted on the rotor and said transmitters being approximately 90° apart.

22. The system of claim 20 where a pair of receivers are mounted on the rotor substantially 180° apart in light conducting sections juxtaposed to light blocked sections of the hollow light conductor mounted on the rotor, four transmitters mounted on the stator said transmitters being approximately 90° apart.

23. The system of claim 1 including means for preventing dust from entering said hollow light conductor.

24. An optical communication link comprising a rotating part and a stationary part,
transmitting and receiving means for transmitting information between said stationary part and said rotating part, said transmitting and receiving means comprising:
a hollow light conductor for transmitting light signals,
means for generating light signals,
means for encoding electrical signals onto said light signals,
means for coupling said encoded light signals to said hollow light conductor for transmission therethrough,
means for receiving said encoded light signals transmitted through at least on part of said hollow optical channel,
means for decoding said received encoded light signals for converting said encoded light signals to electrical signals that are a function of said encoded light signals, and
means for using said electrical signals.

* * * * *